US012806396B2

(12) United States Patent
Densley et al.

(10) Patent No.: US 12,806,396 B2
(45) Date of Patent: Nov. 24, 2026

(54) DIRECT FLUID PATH FOR INLINE DUAL LUMEN PORT

(71) Applicant: Bard Peripheral Vascular, Inc., Franklin Lakes, NJ (US)

(72) Inventors: Bryon Ray Densley, Rochester, MN (US); Ian N. Thomas, West Bountiful, UT (US); Diana Fiumefreddo, Salt Lake City, UT (US); Jessica Hoye, Phoenix, AZ (US); Christian Andersen, Queen Creek, AZ (US)

(73) Assignee: Bard Peripheral Vascular, Inc., Franklin Lakes, NJ (US)

( * ) Notice: Subject to any disclaimer, the term of this patent is extended or adjusted under 35 U.S.C. 154(b) by 293 days.

(21) Appl. No.: 18/575,775

(22) PCT Filed: Jul. 7, 2021

(86) PCT No.: PCT/US2021/040723

§ 371 (c)(1),
(2) Date: Dec. 29, 2023

(87) PCT Pub. No.: WO2023/282898

PCT Pub. Date: Jan. 12, 2023

(65) Prior Publication Data

US 2024/0316327 A1 Sep. 26, 2024

(51) Int. Cl.
*A61M 39/02* (2006.01)

(52) U.S. Cl.
CPC . *A61M 39/0208* (2013.01); *A61M 2039/0211* (2013.01); *A61M 2039/0226* (2013.01)

(58) Field of Classification Search
CPC .............. A61M 2039/0211; A61M 2039/0226
See application file for complete search history.

(56) References Cited

U.S. PATENT DOCUMENTS

| | | | |
|---|---|---|---|
| 4,692,146 | A | 9/1987 | Hilger |
| 4,892,518 | A | 1/1990 | Cupp et al. |

(Continued)

FOREIGN PATENT DOCUMENTS

| | | | |
|---|---|---|---|
| EP | 0963216 | A2 | 12/1999 |
| EP | 3795203 | A1 | 3/2021 |

(Continued)

OTHER PUBLICATIONS

PCT/US2021/040723 filed Jul. 7, 2021 International Search Report and Written Opinion dated May 31, 2022.

(Continued)

*Primary Examiner* — David P. Olynick
(74) *Attorney, Agent, or Firm* — Rutan & Tucker LLP

(57) ABSTRACT

Embodiments disclosed herein are directed to a dual, in-line port having a direct fluid path between the proximal reservoir and the stem. The port includes a conduit extending through the distal reservoir and defining a lumen in fluid communication with the proximal reservoir and the stem. The axis of the conduit lumen is aligned with stem lumen to minimize any tortuous fluid pathway and reduce fluid flow resistance. The port can further include a needle guard extending over the distal reservoir and configured to prevent an access needle from impinging on the conduit when accessing the distal reservoir. Embodiments can further include a removable reservoir insert that defines the distal reservoir.

19 Claims, 15 Drawing Sheets

(56) References Cited

U.S. PATENT DOCUMENTS

| | | | | |
|---|---|---|---|---|
| 5,399,168 | A | 3/1995 | Wadsworth, Jr. et al. | |
| 5,562,618 | A | 10/1996 | Cai et al. | |
| 5,833,654 | A * | 11/1998 | Powers ............. | A61M 39/0208 604/93.01 |
| 7,445,614 | B2 | 11/2008 | Bunodiere et al. | |
| 8,088,112 | B2 | 1/2012 | Chantriaux et al. | |
| 8,267,915 | B2 * | 9/2012 | Daly ................. | A61M 39/0208 604/93.01 |
| 8,277,425 | B2 | 10/2012 | Girard et al. | |
| 8,591,483 | B2 | 11/2013 | Zinn | |
| 8,622,980 | B2 | 1/2014 | Zinn | |
| 9,731,104 | B2 * | 8/2017 | Linden .................. | A61M 39/10 |
| 2005/0075614 | A1 | 4/2005 | Bunodiere et al. | |
| 2009/0156928 | A1 | 6/2009 | Evans et al. | |
| 2011/0098663 | A1 | 4/2011 | Zinn | |
| 2013/0218103 | A1 | 8/2013 | Tallarida et al. | |
| 2017/0128709 | A1 | 5/2017 | Chen | |
| 2017/0197072 | A1 | 7/2017 | Linden et al. | |
| 2019/0298983 | A1 | 10/2019 | Jaroch et al. | |
| 2024/0424277 | A1 | 12/2024 | Andersen et al. | |

FOREIGN PATENT DOCUMENTS

| | | | |
|---|---|---|---|
| WO | 9831417 | A2 | 7/1998 |
| WO | 2005120629 | A1 | 12/2005 |
| WO | 2023282898 | A1 | 1/2023 |
| WO | 2023038634 | A1 | 3/2023 |

OTHER PUBLICATIONS

PCT/US2021/049922 filed Sep. 10, 2021 International Search Report and Written Opinion dated Jun. 15, 2022.

U.S. Appl. No. 18/690,245, filed Mar. 7, 2024 Non-Final Office Action dated Oct. 1, 2026.

* cited by examiner

DIRECT FLUID PATH FOR INLINE DUAL LUMEN PORT

PRIORITY

This application is a U.S. national stage application of International Application No. PCT/US2021/040723, filed Jul. 7, 2021, which is incorporated by reference in its entirety into this application.

SUMMARY

Briefly summarized, embodiments disclosed herein are directed to a dual-reservoir, in-line port having a direct fluid path between the reservoirs and the port stem. Dual, in-line ports can be preferable over side-by-side dual port configurations since the in-line configuration requires a relatively smaller incision site during subcutaneous placement. However, the fluid pathway between the reservoir that is furthest from the stem (the "proximal" reservoir) and the stem lumen can be tortuous. The tortuous fluid pathway can increase fluid resistance or reduce fluid flow. Alternatively, where fluid pathways extend below the reservoir adjacent the stem (the "distal" reservoir), the overall height of the port can be increased, leading to skin stretching or erosion of skin tissues, exposing the port.

Disclosed herein is a vascular access port including, a body including a stem extending longitudinally distally therefrom and defining a first stem lumen and a second stem lumen, a distal reservoir disposed adjacent the port stem and in fluid communication with the first stem lumen, a proximal reservoir disposed adjacent the distal reservoir and in fluid communication with a conduit extending through the distal reservoir to provide fluid communication with the second stem lumen, a septum disposed over one or both of the distal reservoir and the proximal reservoir, and a needle guard extending over the distal reservoir and configured to prevent a needle from contacting the conduit.

In some embodiments, the needle guard extends over a portion of the septum. In some embodiments, the needle guard extends through a portion of the septum. In some embodiments, the needle guard extends under the septum and over the distal reservoir. In some embodiments, an axis of the conduit aligns with an axis of the second stem lumen. In some embodiments, the proximal reservoir is disposed on an opposite side of the distal reservoir from the port stem. In some embodiments, the port stem, the distal reservoir and the proximal reservoir are disposed along a linear axis.

In some embodiments, the vascular access port further includes a housing disposed over one or both of the body and the septum and configured to secure the septum in place over one or both of the distal reservoir and the proximal reservoir. In some embodiments, the housing is formed of a compliant material and over molded onto the body. In some embodiments, the housing is formed of a rigid material and secured to the body in an interference fit, press-fit, or snap-fit engagement. In some embodiments, the vascular access port further includes a base configured to engage the housing and secure one or both of the body and the septum therebetween. In some embodiments, the housing includes one or more septum apertures aligned with one or both of the distal reservoir and the proximal reservoir along a transverse axis, and wherein a portion of the septum extends through the septum aperture. In some embodiments, the body defines a recess configured to receive a reservoir insert therein, the reservoir insert defining the distal reservoir.

Also disclosed is a subcutaneous port system including, a body defining a proximal reservoir and a recess, a reservoir insert defining a distal reservoir and configured to fit within the recess, and a stem including a first lumen in fluid communication with the distal reservoir, and a second lumen in fluid communication with the proximal reservoir.

In some embodiments, the subcutaneous port system further includes a septum disposed over one or both of the proximal reservoir and the distal reservoir. In some embodiments, the subcutaneous port system further includes a housing disposed over one or both of the body and the septum and configured to secure the septum in place over one or both of the proximal reservoir and the distal reservoir. In some embodiments, the reservoir insert includes a conduit extending through the distal reservoir from a first wall to a second wall, opposite the first wall, the conduit defining a conduit lumen configured to provide fluid communication between the proximal reservoir and the second stem lumen. In some embodiments, an axis of the conduit lumen is aligned with an axis of the second stem lumen to provide a straight fluid path between the proximal reservoir and a distal tip of the stem.

In some embodiments, the recess includes a channel disposed in a side wall thereof and extending circumferentially between a proximal conduit aperture, that communicates with the proximal reservoir, and the first stem lumen, the reservoir insert, disposed in the recess, co-ordinates with the channel to define a curved conduit providing fluid communication between the proximal reservoir and the second stem lumen. In some embodiments, the subcutaneous port system further includes an access needle, and a needle guard extending over distal reservoir and aligned with the conduit, the needle guard configured to prevent the needle from contacting the conduit.

Also disclosed is a method of manufacturing a port including, forming a body having a proximal reservoir, a distal reservoir, and a stem, forming a conduit extending from the proximal reservoir, through the distal reservoir, to the stem to provide fluid communication between the proximal reservoir and the stem, forming a needle guard extending over the conduit and configured to prevent a needle from impinging on the conduit, coupling a septum with the body, the septum disposed over one or both of the proximal reservoir and the distal reservoir, and coupling a housing with one or both of the body and the septum to secure the septum to the body.

In some embodiments, the housing defines a septum aperture that aligns with the distal reservoir along a transverse axis, the needle guard coupled with the housing and extending across the septum aperture. In some embodiments, the septum includes a groove extending longitudinally through a top surface thereof, the groove configured to receive the needle guard therein. In some embodiments, the needle guard is formed integrally with the septum, extending therethrough. In some embodiments, the needle guard is coupled with the body, extending from a first edge of the distal reservoir to a second edge of the distal reservoir, opposite the first edge. In some embodiments, the method further includes forming a reservoir insert defining the distal reservoir, the reservoir insert configured to fit within a recess defined in the body, the reservoir insert configured to be removable and replaceable with a second reservoir insert.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1A:
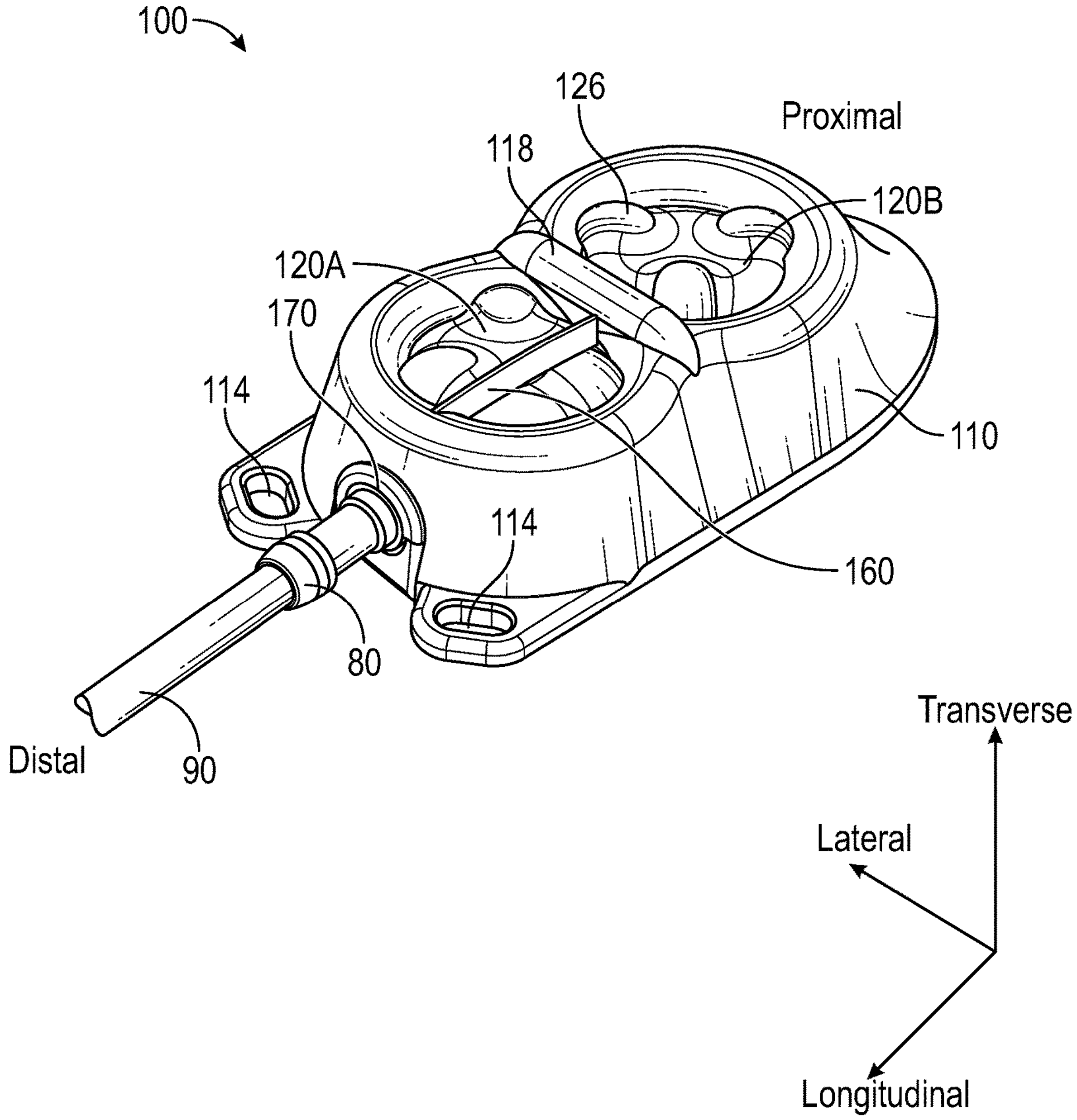
FIG. 1A shows a perspective view of a dual, in-line port having a direct fluid path, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

To assist in the description of embodiments described herein, as shown in FIG. 1A, a longitudinal axis extends substantially parallel to an axial length of the stem 140. A lateral axis extends normal to the longitudinal axis, and a transverse axis extends normal to both the longitudinal and lateral axes. As used herein, a horizontal plane extends along the lateral and longitudinal axes. A vertical plane extends normal to the horizontal plane.

Unless defined otherwise, all technical and scientific terms used herein have the same meaning as commonly understood by those of ordinary skill in the art.

Figure 1B:
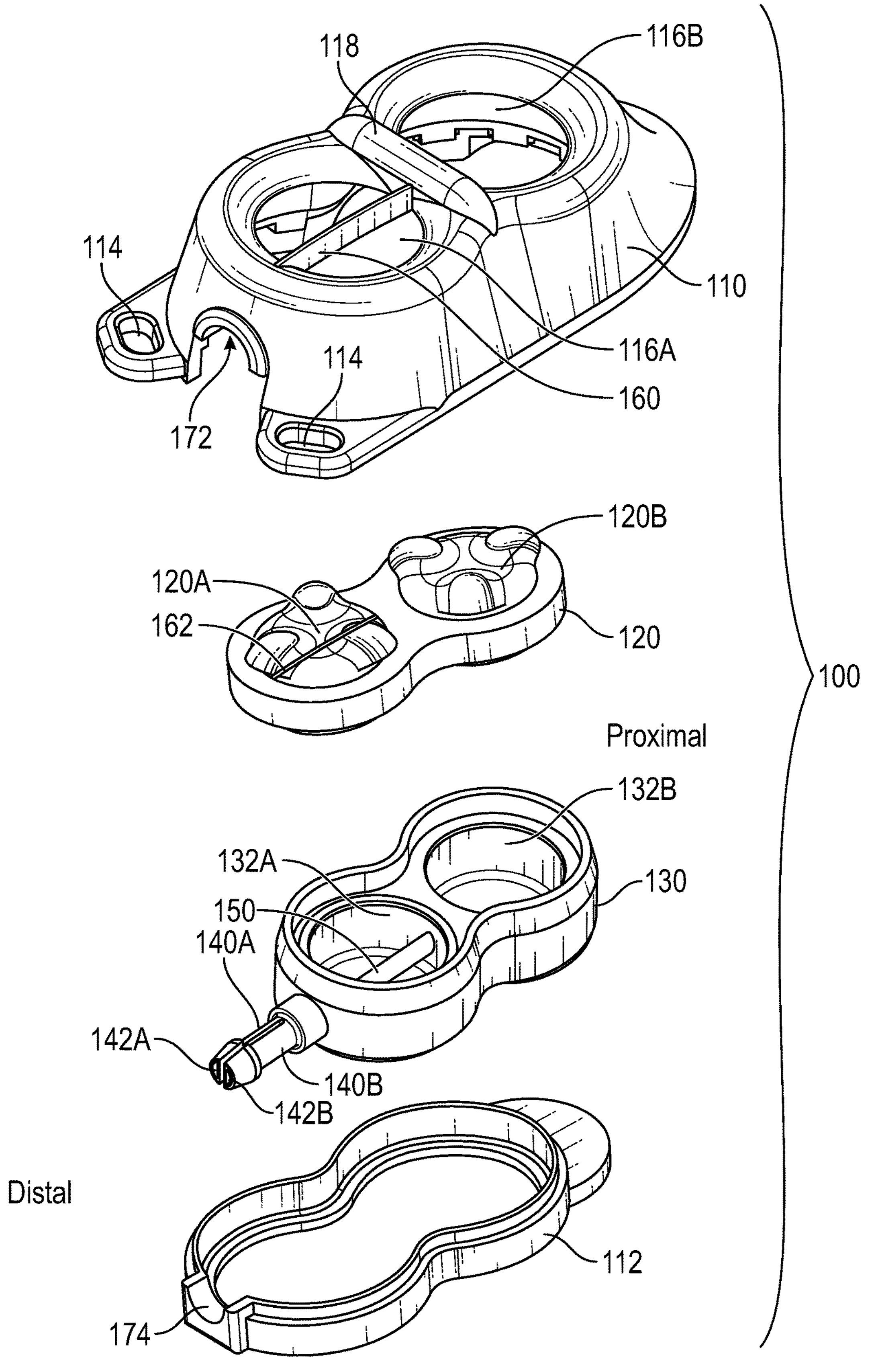
FIG. 1B shows an exploded view of a dual, in-line port having a direct fluid path, in accordance with embodiments disclosed herein.

FIGS. 1A-1B shows a dual, in-line port ("port") 100 having a direct fluid path. The port 100 can generally include a body 130 including a stem 140 extending therefrom, and defining a reservoir 132, e.g. a distal reservoir 132A disposed adjacent the stem 140 and a proximal reservoir 132B disposed adjacent the distal reservoir 132A, opposite from the stem 140. The port 100 can further include a septum 120 disposed over one of the distal reservoir 132A or the proximal reservoir 132B and a body 110 disposed thereover, configured to secure the septum 120 in place relative to the body 130.

The stem 140 can extend along a longitudinal axis and is configured to be coupled to a proximal end of catheter 90. A distal tip of the catheter 90 can be disposed within a vasculature of a patient to provide fluid communication therewith. Optionally, a cathlock 80 can further secure the catheter 90 to the port stem 140. The stem 140 can define a stem lumen 142 in fluid communication with a reservoir 132.

In an embodiment, the body 130 can include a first reservoir, e.g. a distal reservoir 132A, that is in fluid communication with a first stem lumen 142A. A second reservoir, e.g. a proximal reservoir 132B, can be in fluid communication with a conduit 150 defining a conduit lumen 152. The conduit 150 can extend through the first, distal reservoir 132A to provide fluid communication with a second stem lumen 142B. In an embodiment, an axis of the conduit lumen 152 can extend parallel with a longitudinal axis and can align with an axis of the second stem lumen 142B to provide a direct fluid pathway extending between the proximal reservoir 132B and a distal tip of the second stem lumen 142B, as described in more detail herein.

In an embodiment, the port 100 can further include one or more needle-penetrable septa 120. In an embodiment, the port 100 can include a single septum 120 that is disposed over both the distal reservoir 132A and the proximal reservoir 132B. In an embodiment, the port 100 can include a first septum 120A disposed over the distal reservoir 132A, and a second septum 120B disposed over the proximal reservoir 132B. The one or more septa 120 can be configured to provide percutaneous access to the reservoir 132, disposed there below, by an access needle. For example, with the port 100 placed subcutaneously, an access needle can penetrate a skin surface and underlying tissues. The access needle can be urged through the needle-penetrable septum 120, into the reservoir 132 disposed therebelow. The access needle can then provide fluid communication with the reservoir 132.

In an embodiment, as shown in FIGS. 1A-1B and 5A-5C, the port 100 can further include a housing 110 disposed over one of the body 130 or the septum 120 and configured to secure the septum 120 in place relative to the body 130. In an embodiment, the housing 110 can include a rigid, or resilient material such as a plastic, polymer, metal, alloy, composite, combinations thereof, or the like. In an embodiment, the housing 110 can include a compliant material such as a plastic, polymer, elastomer, composite, combinations thereof, or the like.

In an embodiment, the housing 110 can include a base 112. The base 112 can be configured to engage the housing 110 in one of a press-fit, snap-fit, or interference fit engagement. In an embodiment, the base 112 can be coupled to the housing 110 by adhesive, bonding, welding, or the like. In an embodiment, the base 112 can be configured to engage a bottom edge of the body 130 or a bottom surface of the body 130 and secure the body 130 and/or septum 120 between the base 112 and the housing 110. In an embodiment, one of the housing 110 or the base 112 can be over-molded onto one of the body 130 or the septum 120 and can secure the septum 120 in place over the reservoir 132.

In an embodiment, the housing 110 and the base 112 can be formed of the same material. In an embodiment, the housing 110 and the base 112 can be formed of different materials, displaying different mechanical properties. For example, the housing 110 can be formed of a relatively compliant material and the base 112 can be formed of a relatively rigid material. In an embodiment, the housing 110 can include one or more septum apertures 116, for example a distal septum aperture 116A that can align with the distal reservoir 132A along a transverse axis, and a proximal septum aperture 116B that can align with the proximal reservoir 132B along a transverse axis. In an embodiment, a portion of the septum 120 can extend through a septum aperture 116, as described in more detail herein.

In an embodiment, the housing 110 can include a palpation feature 118. The palpation feature 118 can be configured to be palpated by a clinician when the port 100 is placed subcutaneously and indicate a location of one of the distal reservoir 132A or the proximal reservoir 132B. In an embodiment, the housing 110 can include one or more suture holes 114 configured to facilitate securing the port 110 in place, subcutaneously.

In an embodiment, the housing 110 can include a stem aperture 170 aligned with the stem 140. The stem 140 can pass through the stem aperture 170 of the housing 110 to engage the body 130, as described herein. In an embodiment, the housing 110 can include a housing stem recess 172 and the base 112 can include a base stem recess 174. When the base 112 engages the housing 110, the housing stem recess 172 and the base stem recess 174 can co-operate to form the stem aperture 170.

In an embodiment, the port 100 can further include a needle guard 160 extending along a longitudinal axis and configured to prevent an access needle that is accessing the distal reservoir 132A from penetrating the conduit 150. The needle guard 160 can be formed of a needle impenetrable material such as a plastic, polymer, metal, alloy, composite, combinations thereof, or the like. In an embodiment, the needle guard 130 can be formed of the same material as one of the housing 110 or the body 130. The needle guard 160 can extend longitudinally over a portion of the distal reservoir 132A. For example, the needle guard 160 can extend from a proximal edge of the distal septum aperture 116A to a distal edge of the of the distal septum aperture 116A. The needle guard 160 can define a lateral width and a transverse height. In an embodiment, the lateral width of the needle guard 160 can be equal to, less than, or greater than the transverse height. In an embodiment, the needle guard 160 can be formed integrally with the housing 110. In an embodiment, the needle guard 160 can be formed as a separate structure and coupled with the housing 110 using adhesive, bonding, welding, or the like.

Figure 4A:
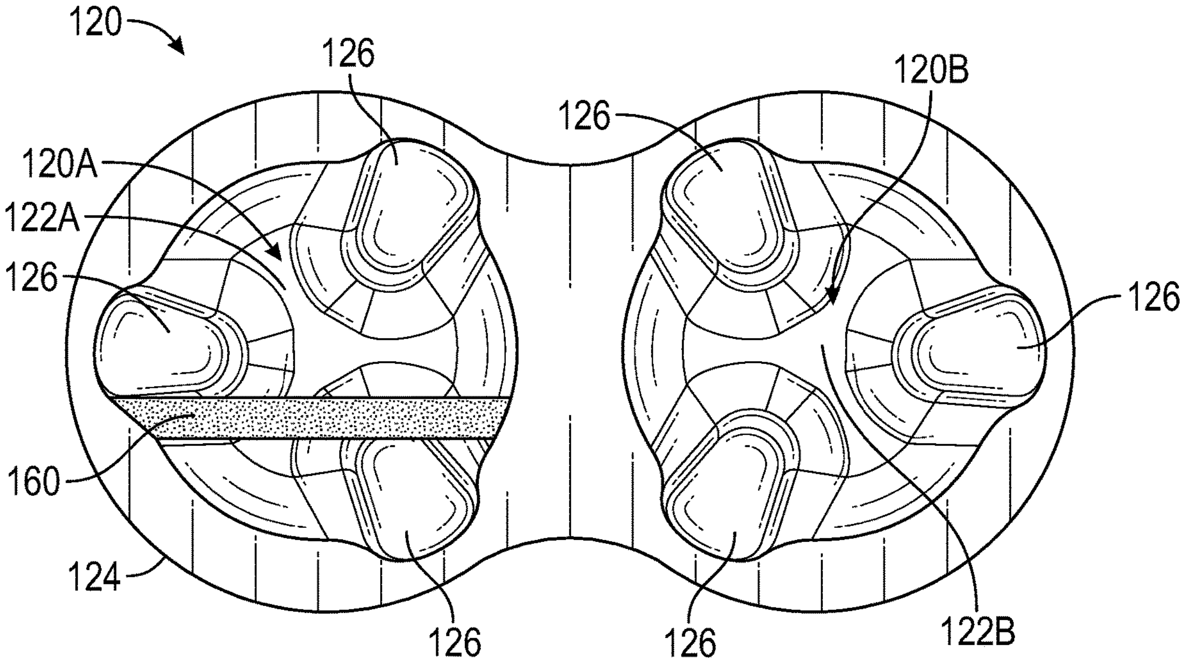
FIG. 4A shows a plan view of a septum of the port of FIG. 1A, in accordance with embodiments disclosed herein.
Figure 4B:
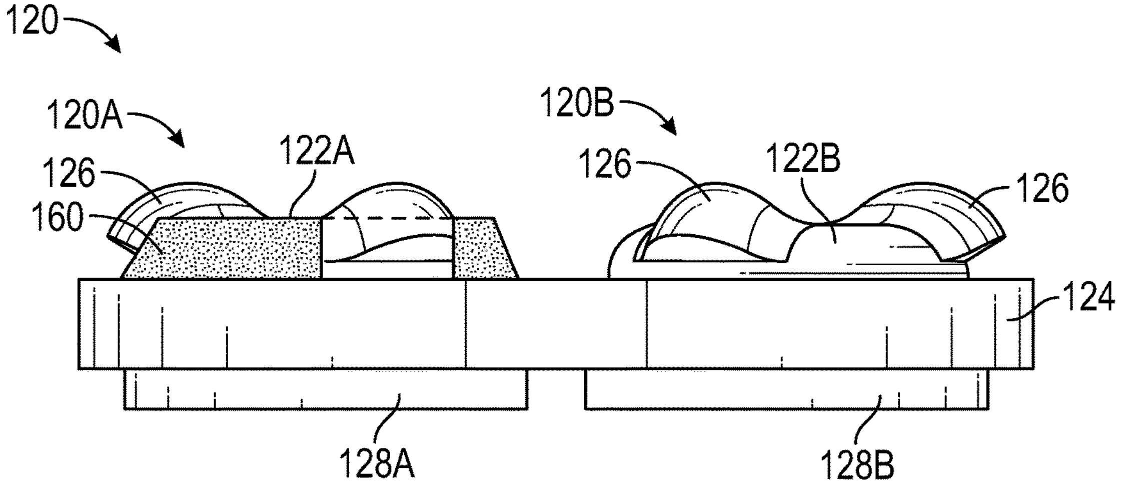
FIG. 4B shows a side view of a septum of the port of FIG. 1A, in accordance with embodiments disclosed herein.
Figure 5A:
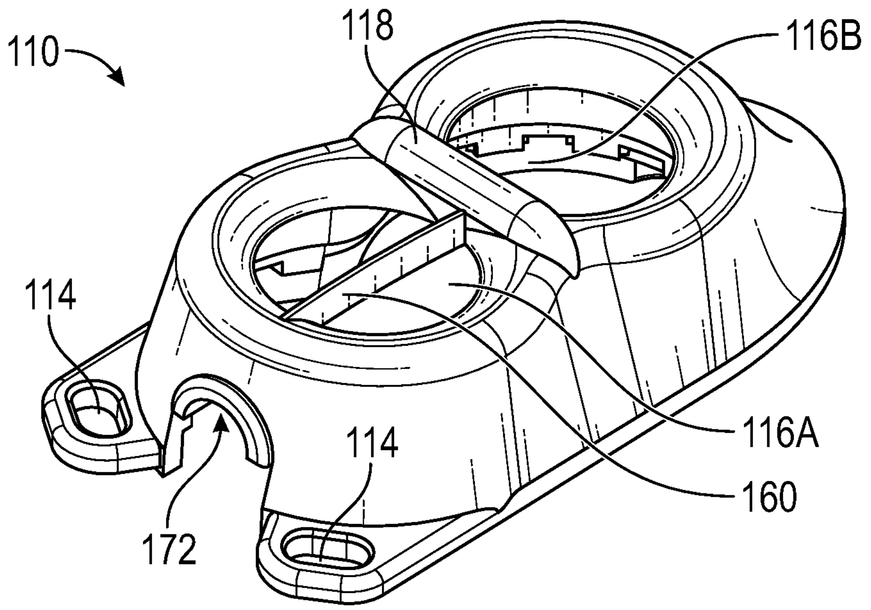
FIG. 5A shows a perspective view of a housing of the port of FIG. 1A, in accordance with embodiments disclosed herein.
Figure 5B:
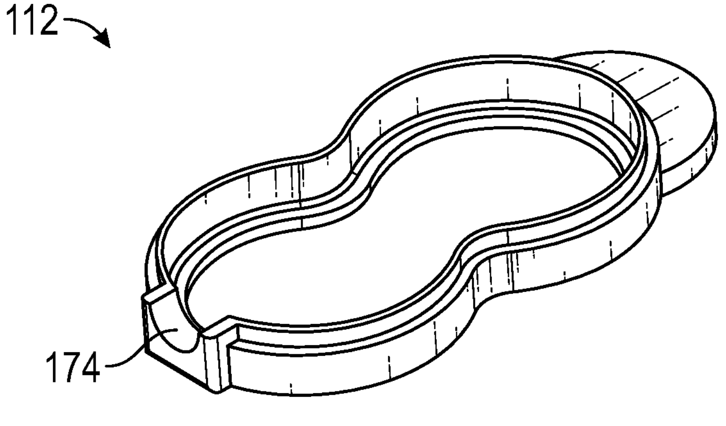
FIG. 5B shows a perspective view of a base of the port of FIG. 1A, in accordance with embodiments disclosed herein.
Figure 5C:
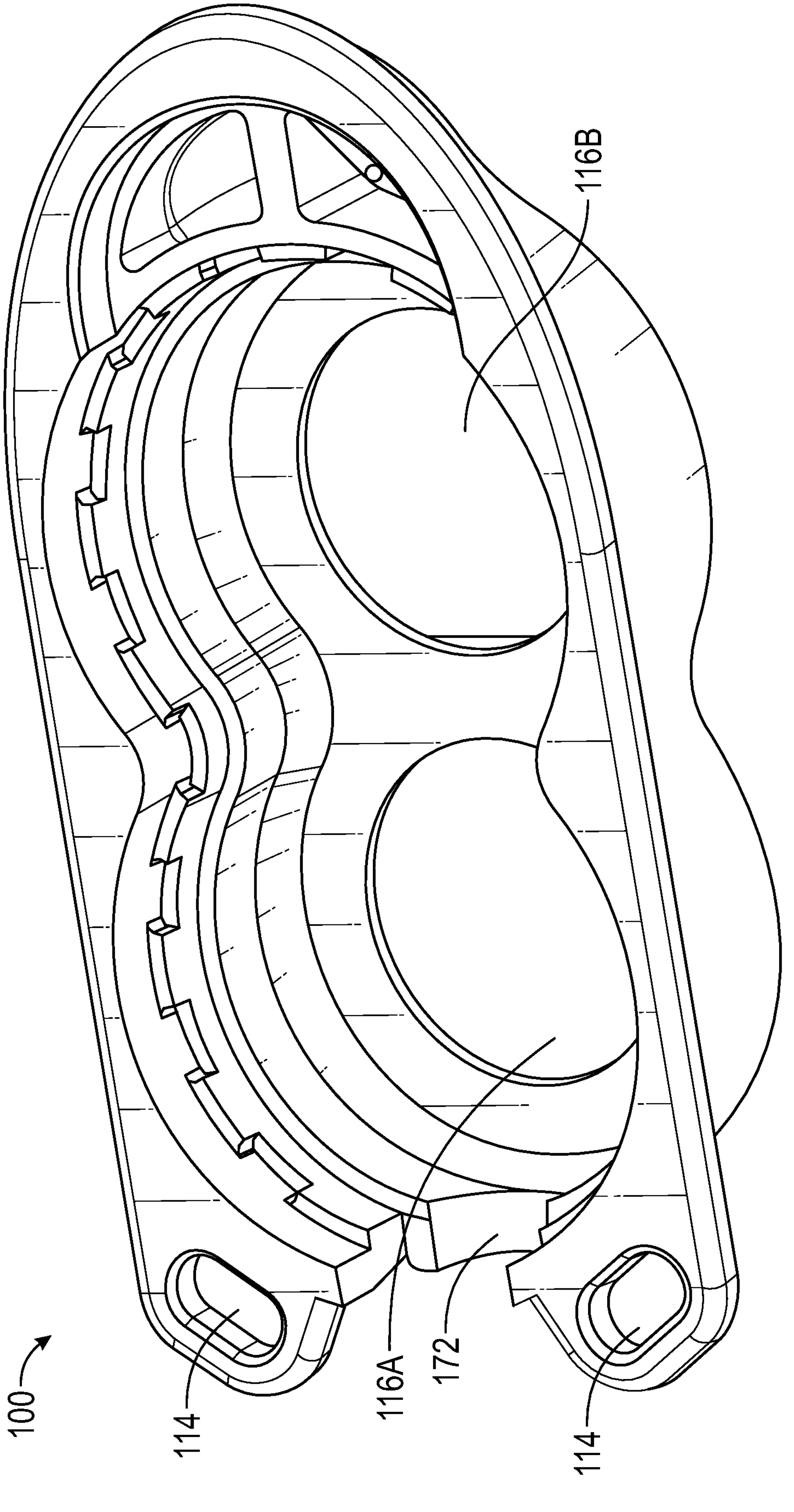
FIG. 5C shows a perspective underside view of a housing of the port of FIG. 1A, in accordance with embodiments disclosed herein.
Figure 6:
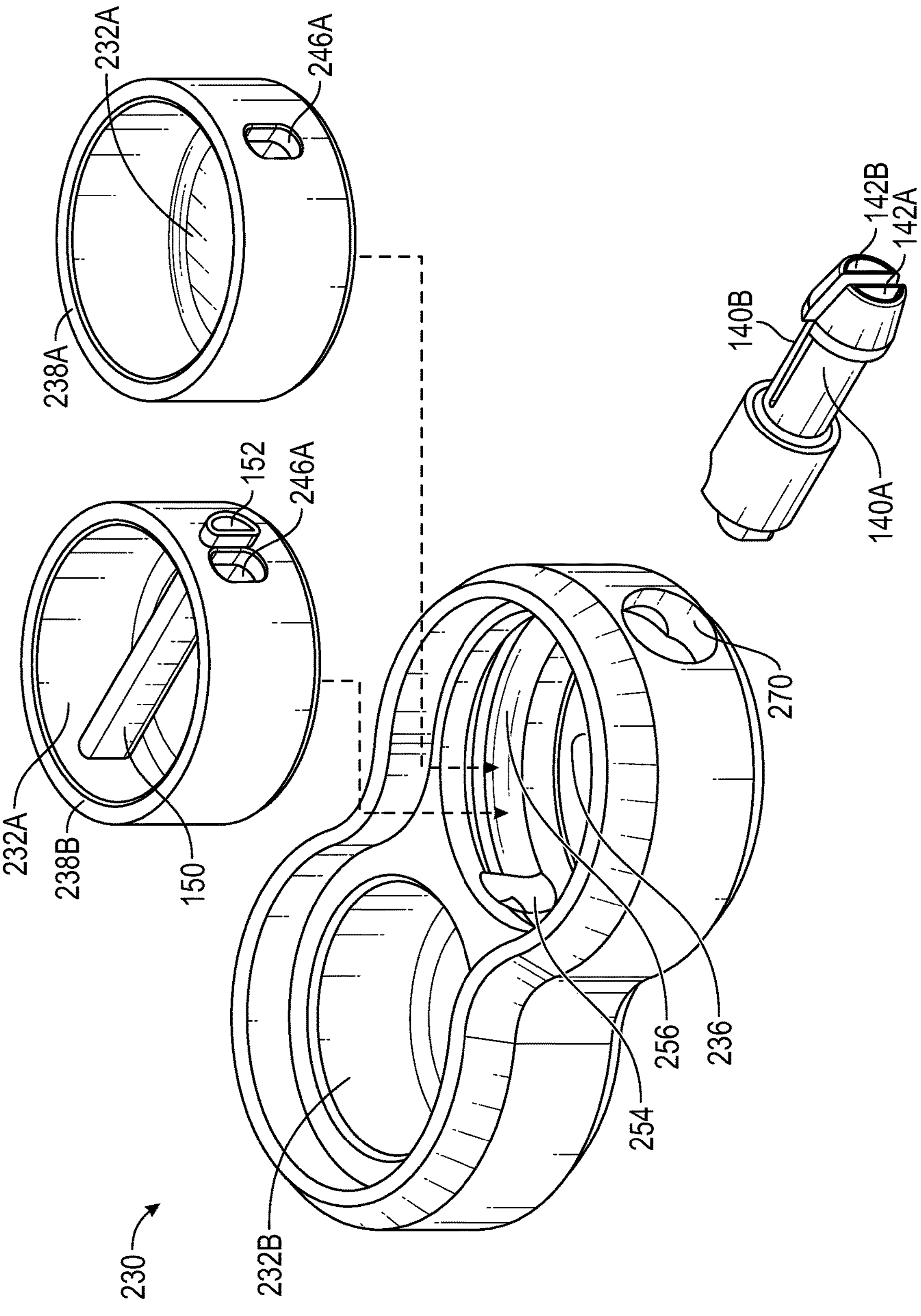
FIG. 6 shows an embodiment of a body of a port having a direct-inline fluid path including a reservoir insert, in accordance with embodiments disclosed herein.

In an embodiment, the needle guard 160 can extend through a portion of the septum 120, for example, through a portion of the distal septum 120A. In an embodiment, the septum 120 can include a groove 162 extending there through and configured to receive the needle guard 160 therein. In an embodiment, as shown in FIGS. 4A-4B, the needle guard 160 can be formed integrally with the septum 120, i.e. the needle guard 160 can be disposed within the septum 120. In an embodiment, the needle guard 160 can be formed of a different material from the septum 120. In an embodiment, the septum 120 can be overmolded onto the needle guard 160.

In an embodiment, the needle guard 160 can extend below the septum 120 and above the reservoir 132. In an embodiment, as shown in FIG. 2F, the needle guard 160 can be formed integrally with the body 130 and can extend over the distal reservoir 132A. In an embodiment, the needle guard 160 can be formed as a separate structure and coupled with the body 130 using adhesive, bonding, welding, or the like.

FIGS. 2A-2F show further details of the body 130 of the port 100. In an embodiment, the body 130 can include a rail 134 extending along a perimeter of the body 130 and extending transversely upwards therefrom. In an embodiment, a perimeter 124 of the septum 120 can fit within the rail 134 and the rail 134 can mitigate lateral or longitudinal movement of the septum 120 relative to the body 130. In an embodiment, the perimeter 124 of the septum 120 can be slightly larger along one of the lateral axis, longitudinal axis, or along an axis extending at an angle therebetween, relative to an inner perimeter of the rail 134. As such, the rail 134 can engage the septum 120 in a press-fit or interference fit, securing the septum 120 in place over the reservoir 132.

Figure 2A:
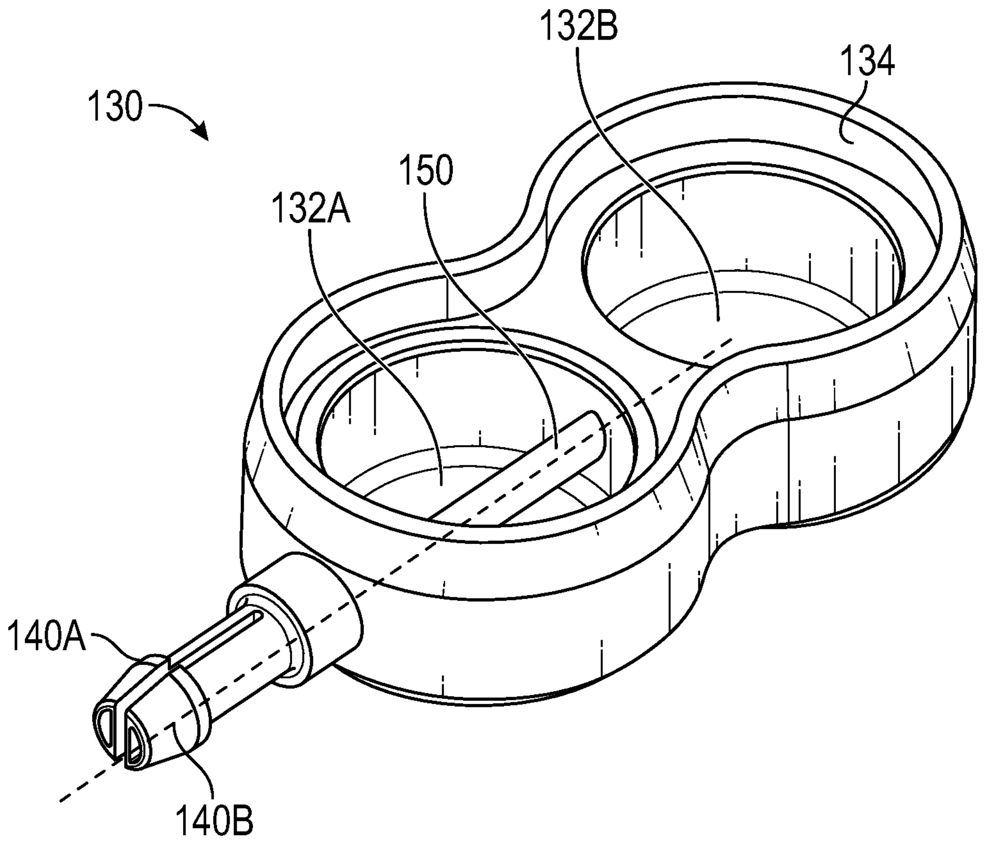
FIGS. 2A-2B show perspective views of a body of the port of FIG. 1A, in accordance with embodiments disclosed herein.
Figure 2B:
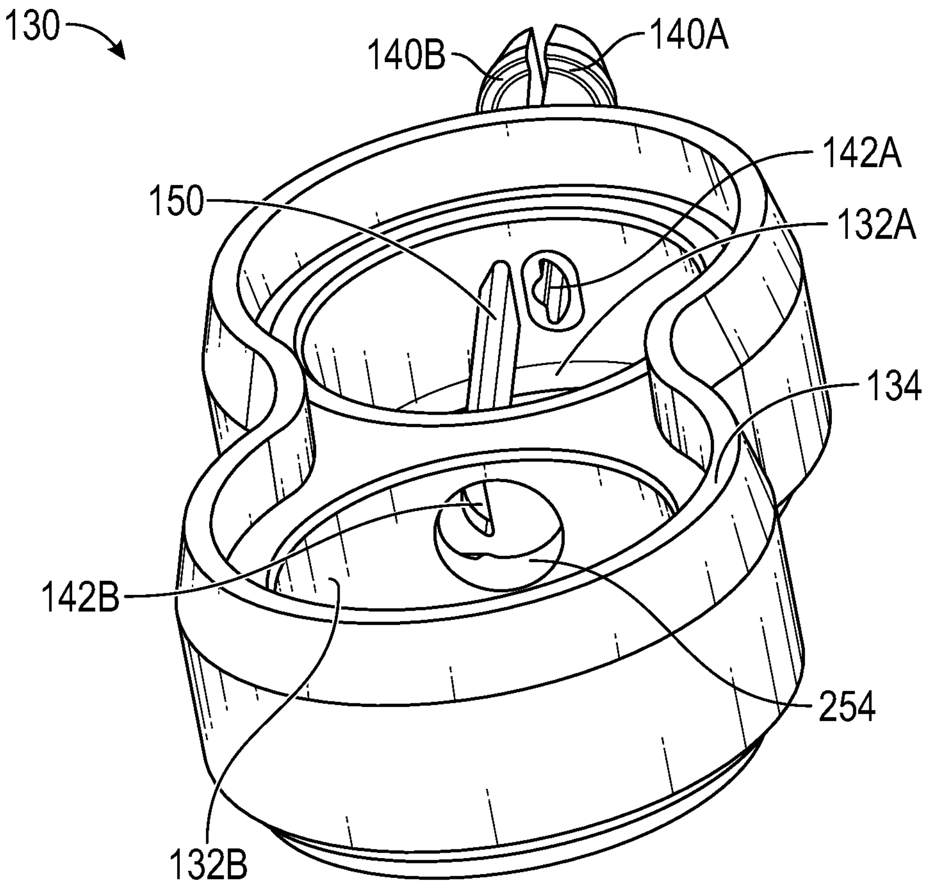
Figure 2C:
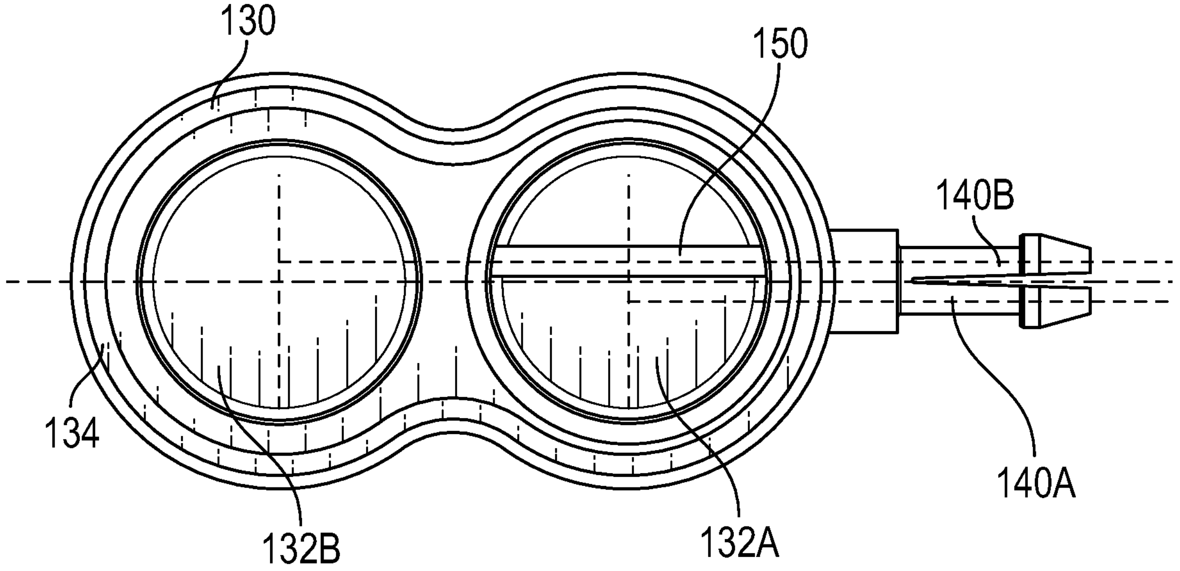
FIG. 2C shows a plan view of a body of the port of FIG. 1A, in accordance with embodiments disclosed herein.
Figure 2D:
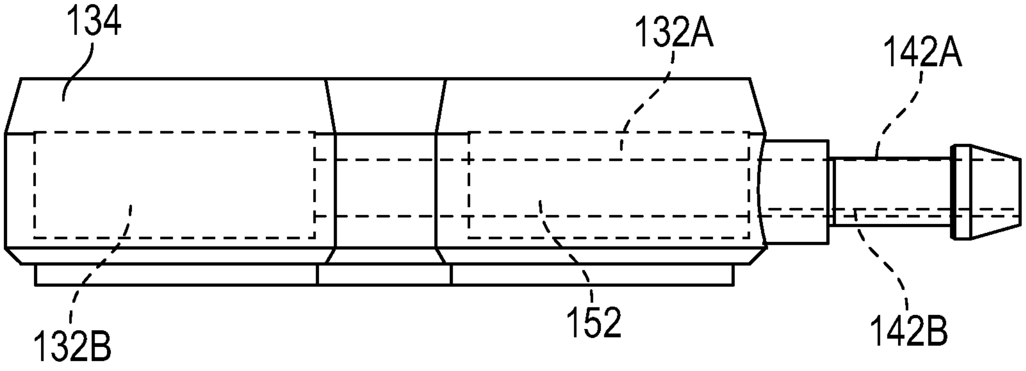
FIG. 2D shows a side view of a body of the port of FIG. 1A, in accordance with embodiments disclosed herein.
Figure 2E:
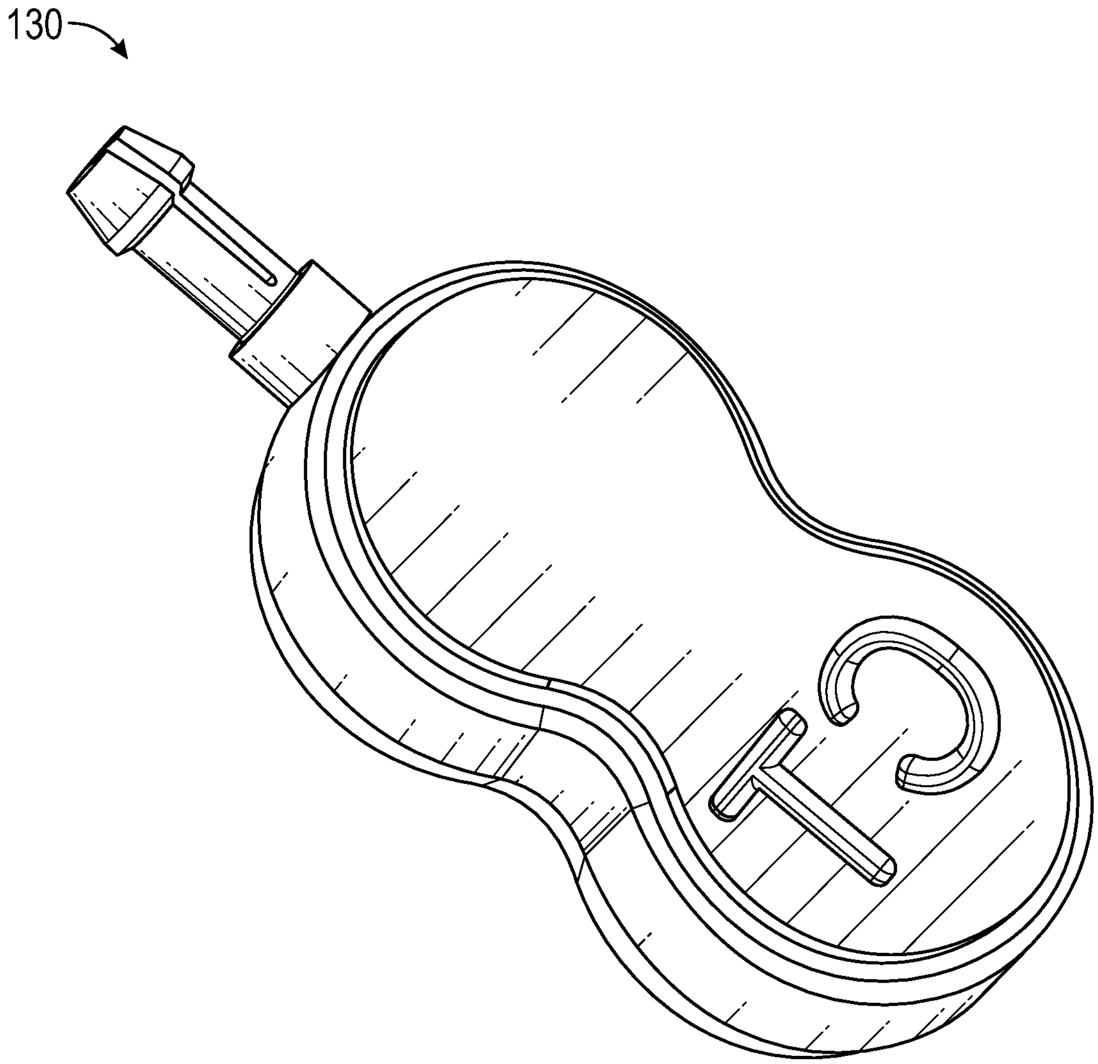
FIG. 2E shows a perspective underside view of a body of the port of FIG. 1A, in accordance with embodiments disclosed herein.
Figure 2F:
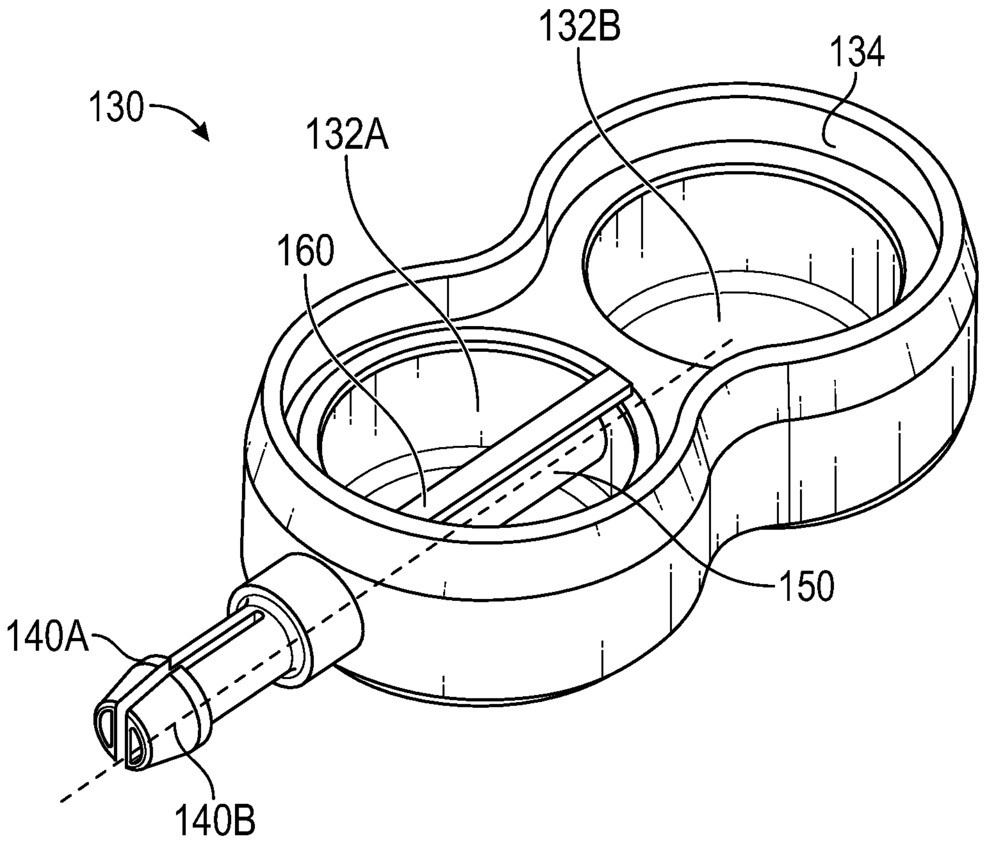
FIG. 2F shows a perspective view of a body of a dual, in-line port having a direct fluid path and including a needle guard, in accordance with embodiments disclosed herein.

In an embodiment, as shown in FIG. 2E, a lower surface of the body 130 can include one or more symbols, alphanumeric symbols, or the like, engraved therein. In an embodiment, a radiopaque or acoustic opaque material can be disposed within the engraved portions so that the symbols can be viewed under medical imaging, when the port 100 is disposed subcutaneously. Advantageously, the symbols can indicate properties of the port 100 (e.g. suitable for C.T., or suitable for high pressure infusion, or the like), or can differentiate between the distal reservoir 132A and the proximal reservoir 132B, or the like.

Figure 3A:
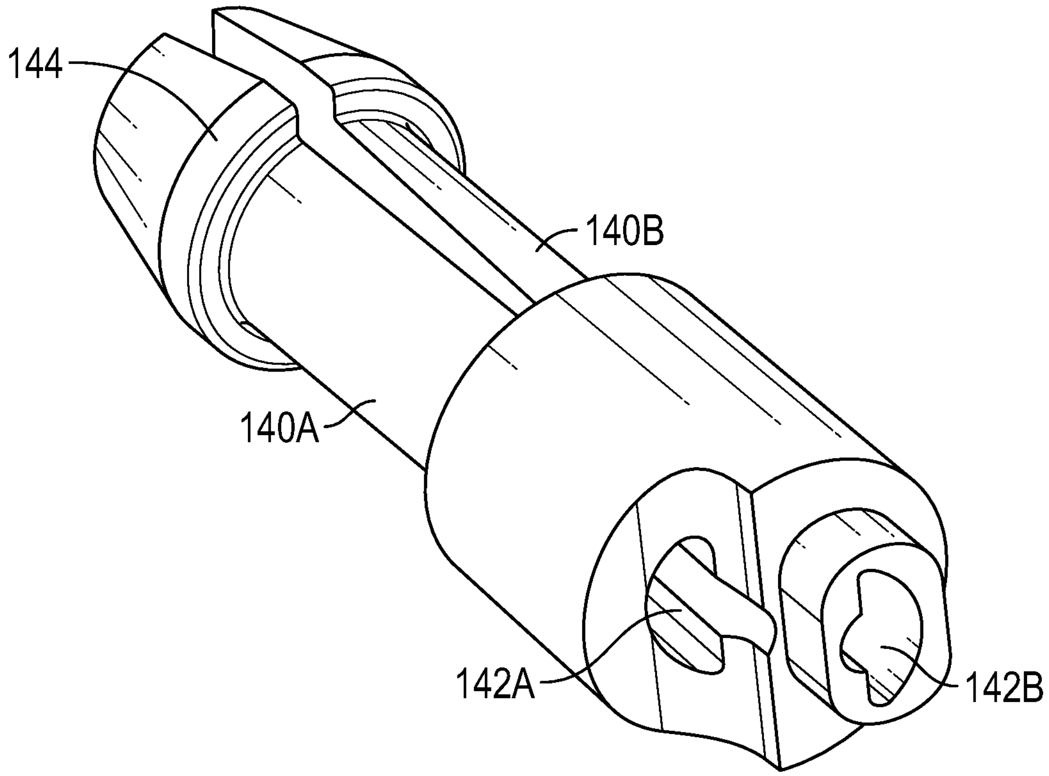
FIG. 3A shows a perspective view of a stem of the port of FIG. 1A, in accordance with embodiments disclosed herein.
Figure 3B:
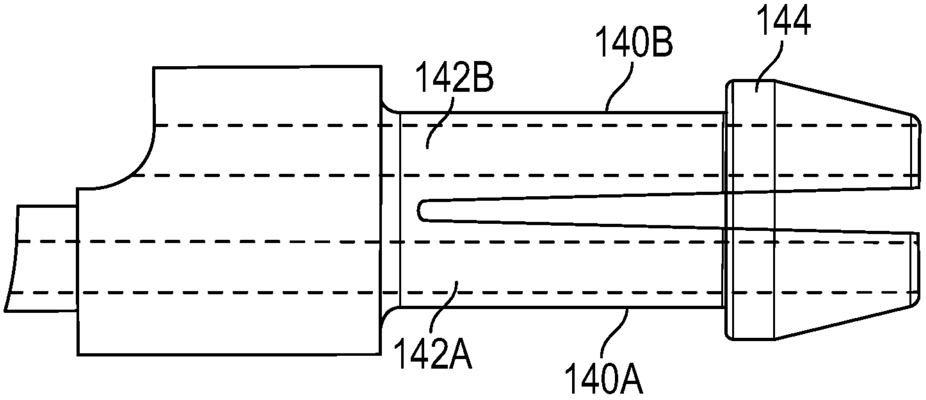
FIG. 3B shows a plan view of a stem of the port of FIG. 1A, in accordance with embodiments disclosed herein.

FIGS. 3A-3B show further details of the stem 140 of the port 100. In an embodiment, the stem 140 can be formed integrally with the body 130. In an embodiment, the stem 140 can be formed as a separate structure and coupled with the body 130 in a press-fit, snap-fit or interference fit engagement, or can be coupled with the body 130 using adhesive, bonding, welding, combinations thereof, of the like. Advantageously, the stem 140 formed as a separate structure and coupled to the body 130 can allow the stem 140 to be exchanged with different sized or configurations of stems to fit different catheters 90, without having to exchange the entire port 100. This can reduce the volume of inventory that is required to be transported and stored, as well as reducing associated costs.

In an embodiment, the stem 140 can define a first stem lumen 142A and a second stem lumen 142B. In an embodiment, the port 100 can include a first stem 140A defining a first stem lumen 142A and a second stem 140B defining a second stem lumen 140B. In an embodiment, the stem 140 can engage a lumen 92 of a catheter 90 in an interference fit, or the like. In an embodiment, an outer surface of the stem 140 can include a barb 144, or similar structure configured to engage the catheter 90 in an interference fit.

In an embodiment, the stem 140 can be configured to engage a dual lumen catheter 90 with a first stem 140A engaging a first catheter lumen to provide fluid communication between the distal reservoir 132A and the first catheter lumen, and a second stem 140B engaging a second catheter lumen to provide fluid communication between the proximal reservoir 132B and the second catheter lumen.

FIGS. 4A-4B show further details of the septum 120 of the port 100. In an embodiment, the septum 120 can define an outer perimeter 124 configured to engage a rim 134 of the body 130, as described herein. As shown in FIG. 4A, a "footprint" or shape of the outer perimeter 124 when viewed from a plan view, can match the shape of the rim 134 of the body 130. For example, the shape of the footprint can represent two converged circles, or a Cassini oval. However, it will be appreciated that other shaped footprints are also contemplated.

In an embodiment, the septum 120 can include one or more upper portions 122 of the septum 120 that can extend transversely upwards to engage one or more septum apertures 116 of the body 110. For example, a distal upper portion 122A can extend transversely upward to engage a distal septum aperture 116A, and a proximal upper portion 122B can extend transversely upward to engage a proximal septum aperture 116B. In an embodiment, the septum 120 can include one or more lower portions 128 that can extend transversely downwards to engage one or more reservoirs 132. For example, a distal lower portion 128A can extend transversely downward to engage a distal reservoir 132A, and a proximal lower portion 128B can extend transversely downward to engage a proximal reservoir 132B. In an embodiment, the lower portion 128 can define a horizontal shape that matches the horizontal cross-section shape of the reservoir 132. As shown, the shape of the lower portion can define a circular shape, however, other shapes are also contemplated. A diameter of the lower portion 128 can be equal to, or slightly less than a diameter of the reservoir 132. Advantageously, the upper portion 122 and the lower portion 128 can co-operate to align the septum aperture 116 with the reservoir 132 along a transverse axis.

In an embodiment, the septum 120 can include one or more palpation features 126 configured to facilitate locating the port 100 when placed subcutaneously. For example, the septum 120 can include a septum palpation feature 126. Similarly, the body 110 can include a body palpation feature 118, as described herein. In an embodiment, the one or more septum palpation features 126 can be disposed on the one or more upper portions 122 of the septum 120 and extend through the septum aperture 116 of the body 110. The palpation features 118, 126 can include one or more protrusions, symbols, alphanumeric symbols, shapes, or the like configured to indicate one of a location of the reservoir 132 disposed therebelow, and/or differentiate between the one or more reservoirs 132, e.g. differentiate between the distal reservoir 132A and the proximal reservoir 132B. In an embodiment, a portion of the upper portion 122, or a portion of the septum palpation feature 126 can extend horizontally outward from a transverse axis to engage a top surface of the body 110. Advantageously, the septum 120 can maintain engagement with the body 110.

In an embodiment, as shown in FIG. 1B, the distal upper portion 122A can include a groove 162 configured to receive the needle guard 160 therein. For example, the needle guard 160 can be coupled with the housing 110 and can extend across a portion of the distal septum aperture 116A. As the housing 110 is assembled with the septum 120 and the body 130, the needle guard 160 can be received within the groove 122 disposed in the septum 120. In an embodiment, as shown in FIGS. 4A-4B, the septum 120 can include the needle guard 160 formed therein and extending through a portion of the septum 120. For example the needle guard 160 can be formed of a different material from that of the septum 120, and display different mechanical properties. The needle guard 160 can be formed within a distal upper portion 122A and aligned with the conduit 150 disposed therebelow. In an embodiment, the needle guard 160 can be formed of a rigid or needle impenetrable material, such as a plastic, polymer, metal, alloy, composite, or the like. The septum 120 can be formed of a compliant, or needle penetrable material, such as silicone rubber or the like. In an embodiment, the needle guard 160 can be formed of the same material as the housing 110.

FIGS. 6-8D show various details of an embodiment of a body 230 that can be used with the port 100. The body 230 can define a proximal reservoir 232B and a recess 236 configured to receive a reservoir insert 238 that defines a distal reservoir 232A. The body 230 can further include a conduit aperture 254 extending through a wall of the body 230, which extends between the proximal reservoir 232B and the distal reservoir recess 236. The conduit aperture 254 can communicate between the proximal reservoir 232B and the recess 236. In an embodiment, the conduit aperture 254 can communicate with a channel 256 disposed in a wall of the recess 236. The channel 256 can extend circumferentially from the conduit aperture 254 to a stem recess 270 disposed opposite the conduit aperture 254 across the recess 236, at a distal end of the body 230.

Figure 7A:
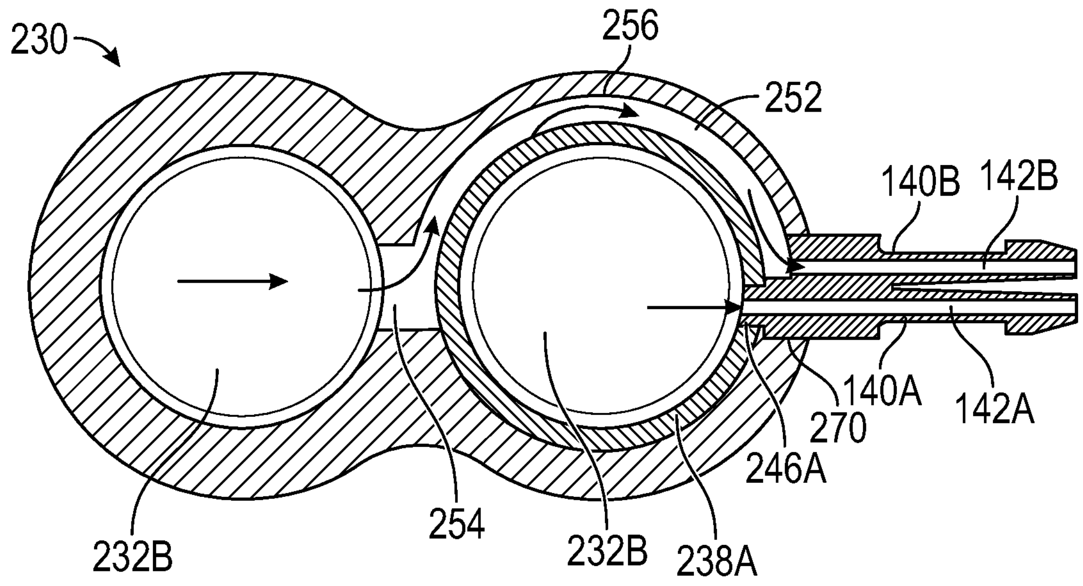
FIG. 7A shows a cross-section plan view of a port having a curved fluid path, in accordance with embodiments disclosed herein.

In an embodiment, a first reservoir insert 238A can define a distal reservoir 232A and a first stem lumen aperture 246A extending through a wall of the first reservoir insert 238A. When the first reservoir insert 238A is disposed within the reservoir recess 236, the first stem lumen aperture 246A can align with a first stem lumen 142A to provide fluid communication between the distal reservoir 232A and the first stem lumen 142A. In an embodiment, a second stem lumen 242B can communicate with the channel 256. In an embodiment, as shown in FIG. 7A, an outer surface of the first reservoir insert 238A can co-operate with the channel 256 to form a curved conduit lumen 252, extending around the distal reservoir 232A and providing fluid communication between the proximal reservoir 232B and the second stem lumen 142B.

In an embodiment, the recess 236 can also be configured to receive a second reservoir insert 238B in place of the first reservoir insert 238A. FIGS. 8A-8D show further details of the second reservoir insert 238B. The second reservoir insert 238B can define a distal reservoir 232A and can include a first stem lumen aperture 246A. The first stem lumen aperture 246A can align with a first stem lumen 142A to provide fluid communication between the distal reservoir 232A and the first stem lumen 142A. In an embodiment, the second reservoir insert 238B can further include a straight conduit 150 defining a lumen 152 and extending through the distal reservoir 232A.

Figure 7B:
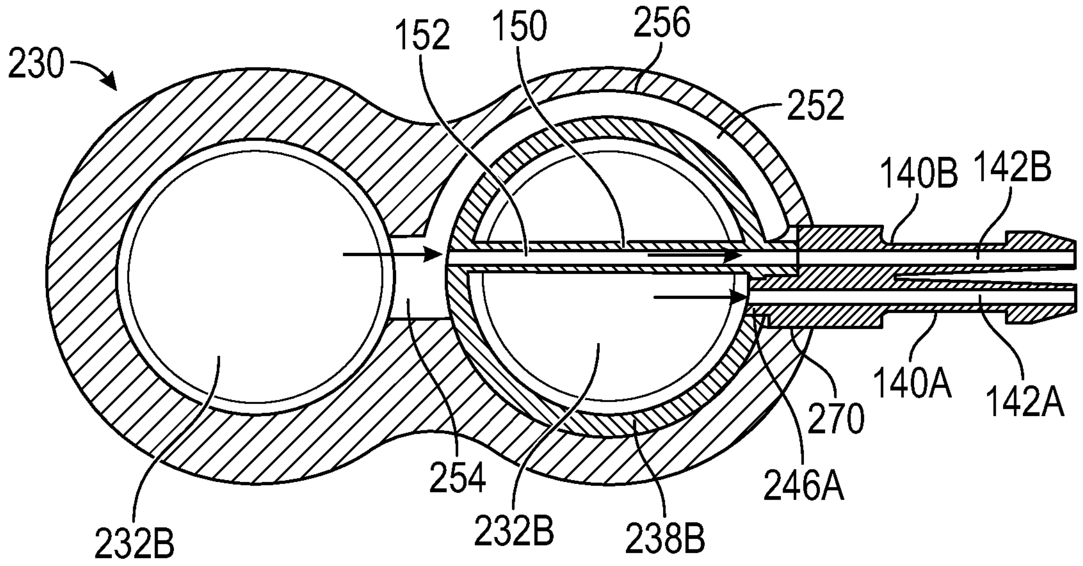
FIG. 7B shows a cross-section plan view of a port having a direct, in-line fluid path, in accordance with embodiments disclosed herein.
Figure 8A:
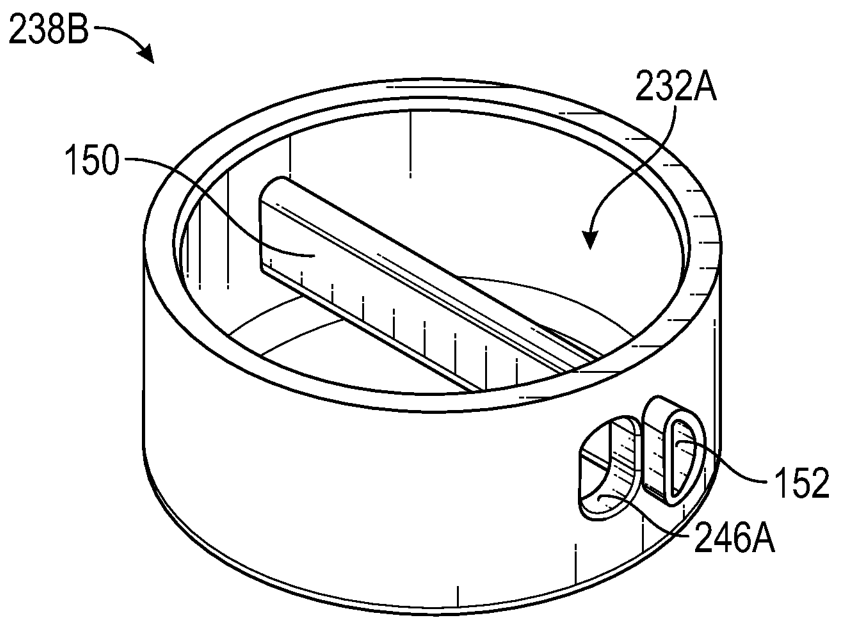
FIGS. 8A-8B show perspective views of a reservoir insert of the port of FIG. 6, in accordance with embodiments disclosed herein.
Figure 8B:
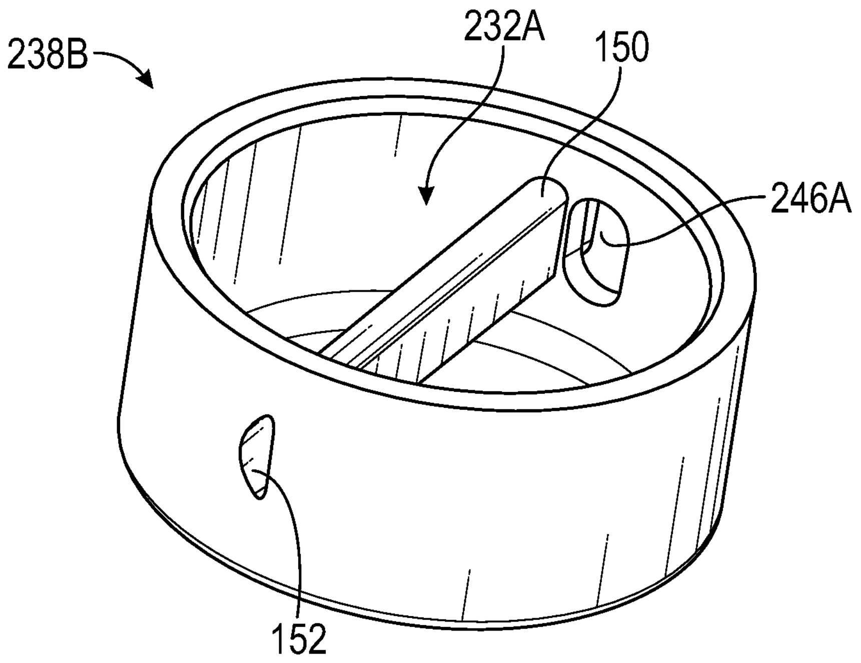
Figure 8C:
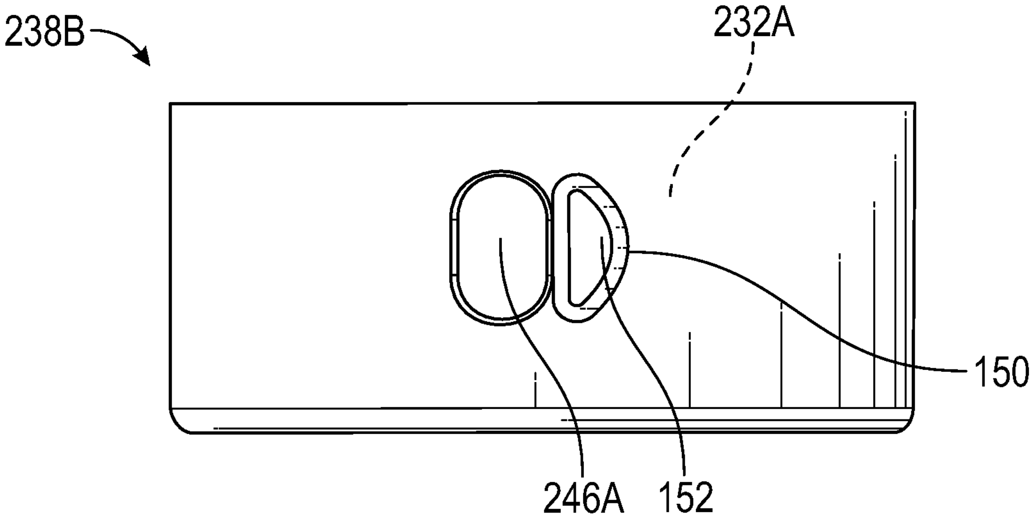
FIG. 8C shows a distal end view of a reservoir insert of the port of FIG. 6, in accordance with embodiments disclosed herein.
Figure 8D:
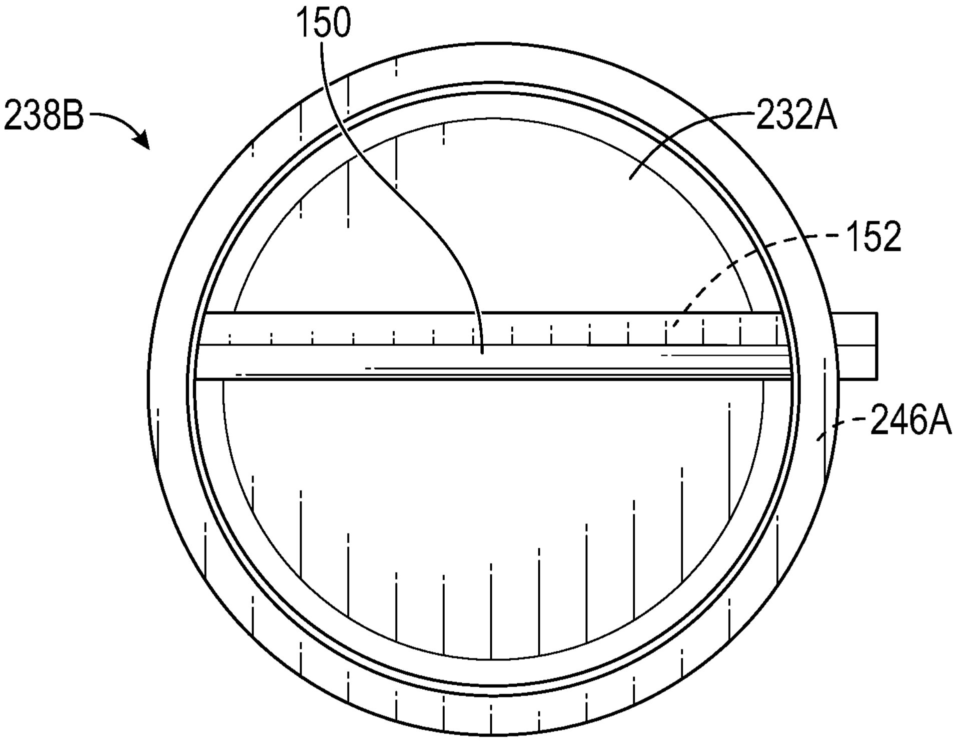
FIG. 8D shows a plan view of a reservoir insert of the port of FIG. 6, in accordance with embodiments disclosed herein.

As shown in FIG. 7B, when the second reservoir insert 238B is received within the recess 236, the straight conduit 150 can provide fluid communication between proximal reservoir 232B and the second stem lumen 142B. To note, a portion of the conduit 150 can extend from an outer surface of the second reservoir insert 238B to occlude the channel 256 and prevent fluid communication therethrough.

As such, the body 230 can be configured to provide a curved conduit lumen 252 extending circumferentially about the distal reservoir 232A. Alternatively the first reservoir insert 238A can be replaced with a second reservoir insert 238B to provide a direct line conduit 150 between the proximal reservoir 232B and the stem 140. Advantageously, the body 230 can be easily reconfigured during manufacturing or assembly with minimal change in parts or assembly tools. This can lead to increased efficiency in inventory and manufacturing, and improve associated costs.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A vascular access port, comprising:

a body including a stem extending longitudinally distally therefrom and defining a first stem lumen and a second stem lumen;

a distal reservoir disposed adjacent the stem and in fluid communication with the first stem lumen;

a proximal reservoir disposed adjacent the distal reservoir and in fluid communication with a conduit extending through the distal reservoir to provide fluid communication with the second stem lumen;

a septum disposed over one or both of the distal reservoir and the proximal reservoir; and a needle guard extending over the distal reservoir and configured to prevent a needle from contacting the conduit.

2. The vascular access port according to claim 1, wherein the needle guard extends over a portion of the septum.

3. The vascular access port according to claim 1, wherein the needle guard extends through a portion of the septum.

4. The vascular access port according to claim 1, wherein the needle guard extends under the septum and over the distal reservoir.

5. The vascular access port according to claim 1, wherein an axis of the conduit aligns with an axis of the second stem lumen.

6. The vascular access port according to claim 1, wherein the proximal reservoir is disposed on an opposite side of the distal reservoir from the stem.

7. The vascular access port according to claim 1, wherein the stem, the distal reservoir and the proximal reservoir are disposed along a linear axis.

8. The vascular access port according to claim 1, further including a housing disposed over one or both of the body and the septum and configured to secure the septum in place over one or both of the distal reservoir and the proximal reservoir.

9. The vascular access port according to claim 8, wherein the housing is formed of a compliant material and over molded onto the body.

10. The vascular access port according to claim 8, wherein the housing is formed of a rigid material and secured to the body in an interference fit, a press-fit, or a snap-fit engagement.

11. The vascular access port according to claim 10, further including a base configured to engage the housing and secure one or both of the body and the septum therebetween.

12. The vascular access port according to claim 8, wherein the housing includes one or more septum apertures aligned with one or both of the distal reservoir and the proximal reservoir along a transverse axis, and wherein a portion of the septum extends through the one or more septum apertures.

13. The vascular access port according to claim 1, wherein the body defines a recess configured to receive a reservoir insert therein, the reservoir insert defining the distal reservoir.

14. A subcutaneous port system, comprising:

a body defining a proximal reservoir and a recess;

a reservoir insert defining a distal reservoir and configured to fit within the recess; and a stem including a first lumen in fluid communication with the distal reservoir, and a second lumen in fluid communication with the proximal reservoir, wherein the reservoir insert includes a conduit extending through the distal reservoir from a first wall to a second wall, opposite the first wall, the conduit defining a conduit lumen configured to provide fluid communication between the proximal reservoir and the second lumen of the stem.

15. The subcutaneous port system according to claim 14, further including a septum disposed over one or both of the proximal reservoir and the distal reservoir.

16. The subcutaneous port system according to claim 15, further including a housing disposed over one or both of the body and the septum and configured to secure the septum in place over one or both of the proximal reservoir and the distal reservoir.

17. The subcutaneous port system according to claim 14, wherein an axis of the conduit lumen is aligned with an axis of the second lumen of the stem to provide a straight fluid path between the proximal reservoir and a distal tip of the stem.

18. The subcutaneous port system according to claim 14, wherein the recess includes a channel disposed in a side wall thereof and extending circumferentially between a proximal conduit aperture, that communicates with the proximal reservoir, and the first lumen of the stem, the reservoir insert, disposed in the recess, co-ordinates with the channel to define a curved conduit providing fluid communication between the proximal reservoir and the second lumen of the stem.

19. The subcutaneous port system according to claim 14, further including an access needle, and a needle guard extending over distal reservoir and aligned with the conduit, the needle guard configured to prevent the access needle from contacting the conduit.

* * * * *